United States Patent [19]

Loch

[11] 4,019,132
[45] Apr. 19, 1977

[54] METHOD AND APPARATUS FOR DETERMINING THE MOISTURE CONTENT OF DIFFERENT KINDS OF MATERIALS

[75] Inventor: Ernst Loch, Uster, Switzerland

[73] Assignee: Zellweger, Ltd., Switzerland

[22] Filed: May 22, 1975

[21] Appl. No.: 579,950

[30] Foreign Application Priority Data

May 22, 1974 Switzerland .................. 7008/74

[52] U.S. Cl. ........................................ 324/65 R
[51] Int. Cl.² ..................................... G01R 27/02
[58] Field of Search .................. 324/65 R, DIG. 1

[56] References Cited
UNITED STATES PATENTS

| 3,287,978 | 11/1966 | Knudsen | 324/DIG. 1 |
| 3,427,537 | 2/1969 | Osborne | 324/65 R |
| 3,493,857 | 2/1970 | Silverman | 324/65 R X |
| 3,588,728 | 6/1971 | Elazar | 324/DIG. 1 |
| 3,680,384 | 8/1972 | Gridheim | 324/DIG. 1 |
| 3,688,581 | 9/1972 | LeQuernec | 324/DIG. 1 |
| 3,766,471 | 10/1973 | Pullman | 324/65 R |

Primary Examiner—Stanley T. Krawczewicz
Attorney, Agent, or Firm—Craig & Antonelli

[57] ABSTRACT

A method and apparatus for determining the moisture content of different kinds of materials wherein electrodes having a voltage supplied thereto are applied to the material to be tested for providing a measuring current corresponding to the moisture content of the material. The measuring current is applied to an amplifier having a low-valued input resistance and the moisture content is determined by adjusting a scale graduated in moisture values in accordance with the output of the amplifier. A balancing device is provided for balancing the output of the amplifier and the scale is connected to the balancing device to indicate a balance position as the moisture content value. The amplifier is also provided with a device for converting the measuring current to a voltage corresponding to the logarithm of change in current and a device for providing temperature compensation.

24 Claims, 8 Drawing Figures

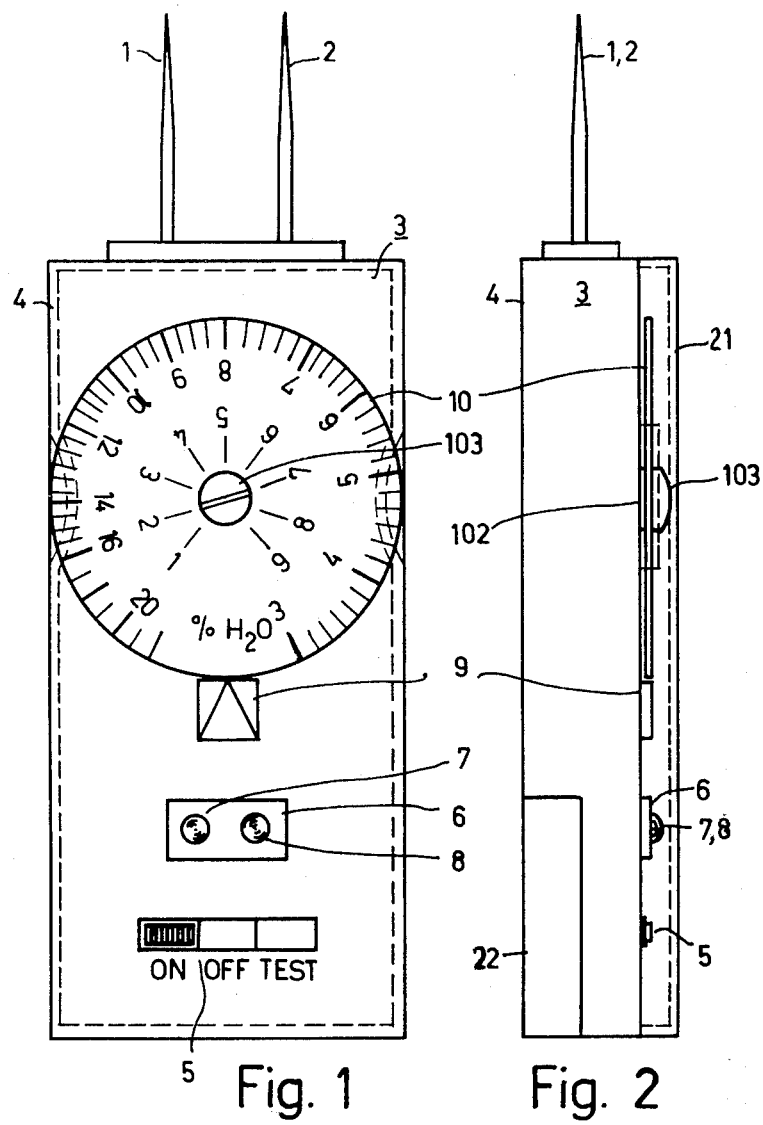
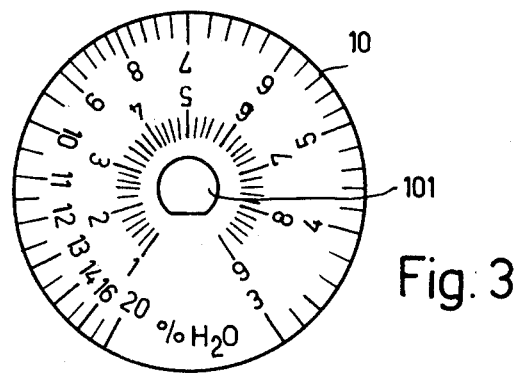
Fig. 1   Fig. 2
Fig. 3

METHOD AND APPARATUS FOR DETERMINING THE MOISTURE CONTENT OF DIFFERENT KINDS OF MATERIALS

The present invention relates to a method and apparatus for determining the moisture content of different kinds of materials.

Conventional moisture gauges, which function on the conductivity principle, use at the input end a voltage divider consisting of the variable, moisture-dependent resistance of the material to be measured in series with a very high-valued reference resistance. Measurement of the component voltage representing the moisture content requires a vacuum tube amplifier or an FET-amplifier with an input resistance value tending toward infinity. These amplifiers with their extremely high input resistances have provide well known technical difficulties, such as instability, the appearance of hum voltages and static charges. Such a circuit arrangement also provides considerable inaccuracies which limit the useful measuring range both with very high and with very low division ratios of the measuring voltage.

It is therefore an object of the present invention to obviate the aforementioned disadvantages of the prior art arrangements.

In accordance with the present invention, there is provided a method for determining the moisture content of different kinds of materials by measuring their conductivity by bringing into contact with the material to be measured a pair of electrodes across which a voltage is connected, applying the current flowing in this circuit to an amplifier having a low-valued input resistance and determining the moisture content of the material by adjusting a voltage device having a scale graduated in moisture values until the output of the amplifier is balanced, at which point the moisture value of the material can be read from the graduated scale.

The apparatus according to the present invention, includes electrodes which are connectible to a voltage source and which are arranged to be applied to the material to be tested, an amplifier connected with the electrodes and having a low-valued input resistance and an adjustable scale graduated in moisture values.

The method and apparatus of the present invention is based on a circuit arrangement which eliminates the need for the voltage divider of prior art arrangements referred to above. The circuit according to the present invention processes the current which is determined by the material being measured when a voltage is applied to it through suitable electrodes and the low-valued input resistance of the amplifier automatically eliminates the disturbing influences referred to above. In addition, the circuit is designed in such a way that a voltage which changes with the logarithm of the input current is formed at the output of the amplifier. By eliminating the voltage divider which limits the measuring range and through the logrithmic dependence of the current-voltage characteristic, it is possible to obtain a virtually unlimited measuring range without any need for connections to be changed. In addition, the logarithmic measured value provides for an extremely favorable configuration of the measuring scale. The scale can be designed for replacement and for individual use with different materials, so that the instrument may readily be adapted to materials with different characteristics.

Input circuits of the type described above with a low-valued input resistance and a logarithmic current voltage dependence are known in the art and may be formed, for example, by operational amplifiers and suitably wired transistors, dividers and the like.

In an advantageous embodiment of the present invention, the indicating device is based on a zero balance arrangement. Accordingly, there is no need to use an indicating instrument. Balance is instead obtained by setting a potentiometer which may be directly connected to a dial graduated in moisture values. In addition, the measuring method with zero adjustment enables an indication to be obtained both for the as yet non-definitive adjustment and also for the direction of the mis-alignment by means of control lamps. In addition, it is possible by using an error-evaluating circuit known per se to obtain automatic zero balance by virtue of the fact that, in the event of non-definitive balance, the error signal may be used via amplifying means for trimming the balancing potentiometer.

These and other objects, features and advantages of the present invention will become more apparent from the following description when taken in connection with the accompanying drawings which show, for purposes of illustration only, several embodiments in accordance with the present invention, and wherein:

FIG. 1 is a plan view of an apparatus according to the present invention,

FIG. 2 is a side elevation of the apparatus of FIG. 1,

FIG. 3 shows a dial,

Figure 4:
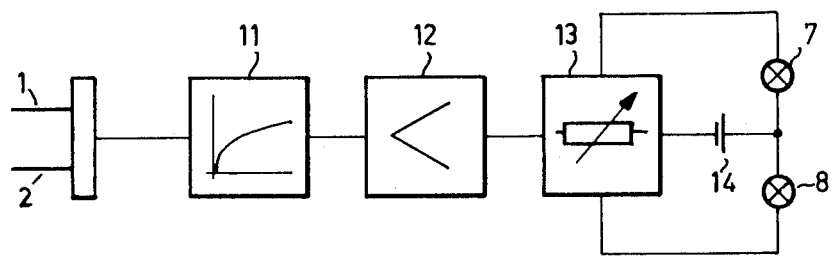
FIG. 4 is a block circuit diagram of a system arrangement with manual balance.

Referring now to the drawings wherein like reference numerals are utilized to designate like parts throughout the several views there is shown in FIG. 1, a measuring apparatus in plan view including, electrodes 1 and 2 which have to be brought into intimate contact with the material to be measured. In the case of textile materials, for example, the electrodes 1, 2 may (as illustrated) be in the form of needles which penetrate into correspondingly deep zones of the material. In the case of sheet-form materials, the electrodes have to be in the form of plates. Alternatively, they may be in the form of sleeves which surround the material to be measured.

The electrodes 1, 2 are either fixed to the actual measuring instrument 3 by means of plug-and-socket connections, or alternatively may be connected to the measuring instrument in a known manner through flexible leads.

The measuring instrument 3 includes a housing 4 having at the front face thereof those components required for operation of the device namely, an operating switch 5 for switching the instrument on, an indicating element 6, with two control lamps 7 and 8, a pointer 9 and a dial 10 having moisture values indicated thereon in percentage values. The diameter of the dial 10 is preferably such that its edge projects beyond the edge of the housing, on one side at least, so that it can be turned by a finger. The front is advantageously protected by means of a transparent cover 21. This cover can be seen in FIG. 2. FIG. 2 also shows a removable cover 22 which closes a battery housing for accommodating a battery responsible for the supply of current.

The dial 10 shown in FIG. 3 is formed with a central hole 101 designed in such a way that the dial can only be fitted on in one direction relative to the shaft 102. It is held in position for example by means of a screw 103 or in any other suitable manner. The housing cover 21 may, for example, be designed in such a way that, when the cover is removed, the dial may be removed from the shaft 102 without any need for tools, whereas, when the cover is in position, the dial is held firmly on the shaft. In cases where the symmetry or the shape of the hole 101 intended for orientation is axially symmetrical, the dial 101 may be used on both sides, thus making it possible to reduce the required number of dials calibrated for different materials.

FIG. 4 is a block diagram of a system arrangement according to the present invention employing manual balance. The electrodes 1 and 2 are connected to an input circuit 11 having a logarithmic current-voltage characteristic, which circuit is connected to an amplifier 12. A battery 14, which is accommodated in the battery housing 22, serves for supplying power to the system. A balancing potentiometer circuit 13 is connected in such a way that upon adjustment to one side of the balance point one of the two control lamps will be illuminated, for example the control lamp 7, while the other control lamp 8 is not energized. If the potentiometer is turned slightly in the opposite direction to the other side of the balance point, the control lamp 8 is energized and the control lamp 7 goes out. There is no neutral range in which both the control lamps 7 and 8 are either out or on at the same time. However, it is possible to read off sufficiently accurate moisture values with this method of indication. The dial 10 is coupled with the potentiometer so that the position of the pointer 9 is indicative of the balance position. In addition to its "on" position, the operating switch 5 also has a "test" position. In this position, such voltages are applied to the indicating and balancing members that predetermined graduation points on an auxiliary scale on the dial 10 are adjusted to determine whether the instrument is ready for operation.

Figure 7:
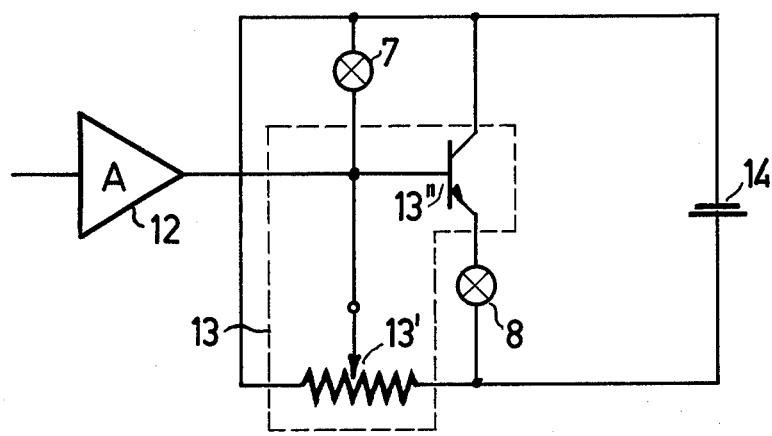
FIG. 7 is a schematic circuit of diagram of the balancing arrangement of FIG. 4.

FIG. 7 is a schematic diagram of the balancing arrangement of FIG. 4 wherein the balancing potentiometer circuit 13 includes a potentiometer 13' and a transistor 13" connected to the indicator lamps 7 and 8, the battery 14 and the output of the amplifier 12 such that depending upon the position of the slider of potentiometer 13', either the base of the transistor 13" is a positive potential with respect to the emitter so that lamp 7 is dark and lamp 8 has full battery voltage applied via the conducting transistor 13" or the base of the transistor is at negative potential with respect to the emitter with lamp 7 being at full battery voltage and lamp 8 dark due to the transistor 13" being cut off.

Figure 5:
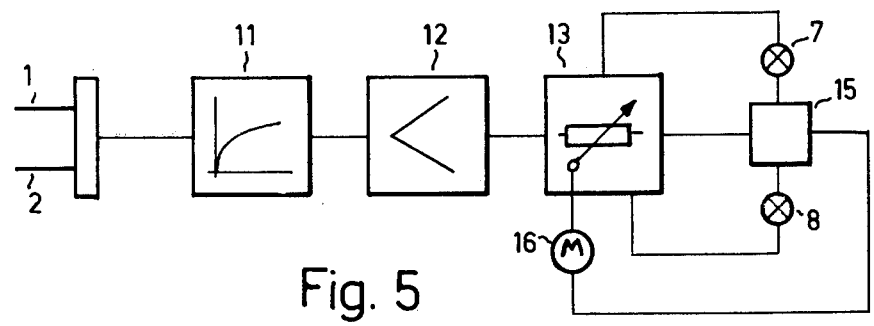
FIG. 5 is a block circuit diagram of a system arrangement with automatic balance.

FIG. 5 shows a modification of the measuring instrument with automatic balance. The control lamps 7 and 8 which monitor balance are supplemented by a discriminator 15 which, when the instrument is not balanced, evaluates the current feeding the control lamps 7 and 8 in such a way that the balancing potentiometer is moved in the direction of the increasing balance. This can be done, for example, by means of a motor 16 which is coupled to the potentiometer circuit 13. However, it is also possible to use purely electrical balancing means completely free from mechanical adjusting elements. However, automatic balancing moisture gauges of this kind can no longer be used as pocket instruments, instead they are used as permanently installed monitoring instruments with corresponding control and regulating functions, for example, in drying installations.

Figure 8:
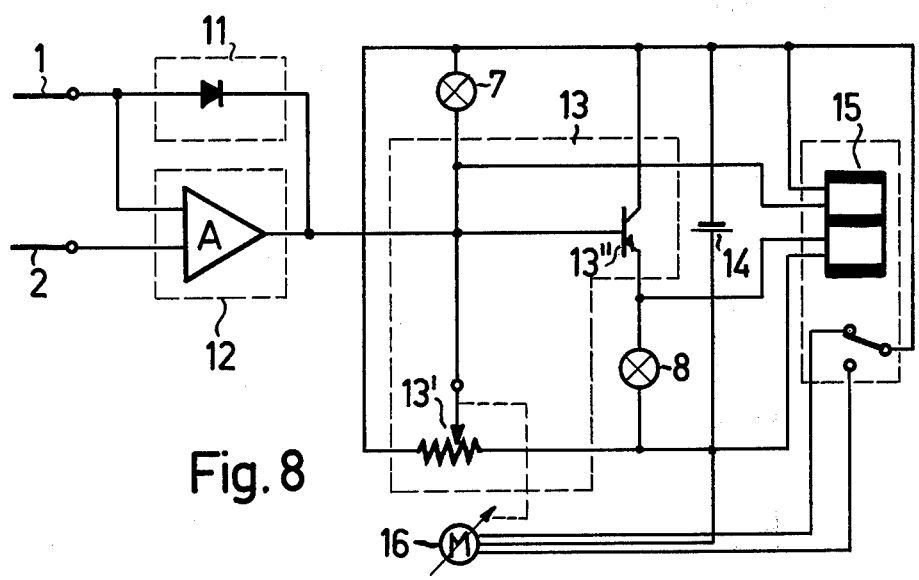
FIG. 8 is a schematic circuit diagram of the system of FIG. 5.

FIG. 8 is a schematic diagram of the block diagram system arrangement of FIG. 5 wherein the logarithmic current voltage characteristic is provided by the input circuit 11 in the form of a diode arranged in the negative feedback path of the operational amplifier 12 having a low valued input resistance which may be on the order of 0.01 to 1 Ohms and having the electrodes 1 and 2 connected to the input thereof. The Figure balancing arrangement corresponds to FIG. 7 with the addition of a discriminator 15 in the form of a differential relay and a balancing motor 16. The windings of the relay are connected in parallel to the indicator lamps 7 and 8 such that in accordance with the voltage applied to lamp 7 or 8, the upper or lower winding of relay 15 is energized. Consequently, the double throw switch of the relay is in one or the other position energizing motor 16 in the appropriate direction and displacing the slider of the potentiometer 13'.

Figure 6:
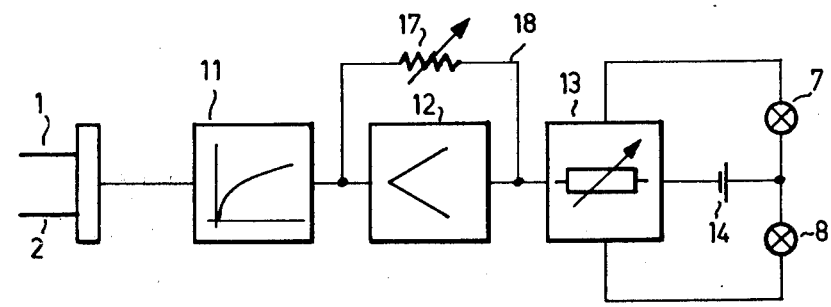
FIG. 6 is a block circuit diagram of a modified embodiment of the arrangement shown in FIG. 4 or 5 with temperature compensation.

The measuring circuit is governed to a certain extent by temperature. Accordngly, the measuring instrument advantageously incorporates temperature compensation for determining relative moisture content. FIG. 6 shows an exemplary arrangement of this type wherein the amplifier 12 is connected to a feedback path 18 incorporating a temperature sensitive element 17. Corresponding to the temperature characteristic of this element 17, the output of the amplifier is made dependent upon the temperature prevailing at the point of use. However, other methods known per se may be used for compensating the dependence upon temperature.

While we have shown and described several embodiments in accordance with the present invention, it is understood that the same is not limited thereto but is susceptible of numerous changes and modifications as known to those skilled in the art, and we therefore do not wish to be limited to the details shown and described herein but intend to cover all such changes and modidications as are encompassed by the scope of appended claims.

I claim:

1. A method for determining the moisture content of different kinds of materials by measuring their conductivity comprising the steps of passing an electrical measuring current through the material whose moisture content is to be measured, detecting said measuring current which is indicative of the conductivity of the material, directly coverting the measuring current into a measuring voltage corresponding to the logarithm of said current, applying the measuring voltage to an amplifier having a low-valued input resistance, and determining the moisture content of the material by adjusting a scale graduated in moisture values in accordance with the output of the amplifier.

2. A method according to claim 1, wherein the step of determining the moisture content includes adjusting a device connected to said scale providing a variable voltage until a zero balance of the output of the amplifier is obtained.

3. A method according to claim 2, including indicating deviations from the zero balance position in either of two directions therefrom by at least one indicting element.

4. A method according to claim 1, wherein the step of determining the moisture content includes manually adjusting a device for producing a voltage balancing the output of the amplifier.

5. A method according to claim 4, wherein the balancing device includes a potentiometer and the scale is adjusted to indicate the moisture value in accordance with the balance position of the potentiometer.

6. A method according to claim 2, wherein the balancing device includes a potentiometer having the graduated scale coupled to a movable member thereof, and automatically adjusting the movable member of the potentiometer to a balance position.

7. A method according to claim 4, including utilizing individually graduated scales for different kinds of material to be tested.

8. A method according to claim 2, including utilizing individually graduated scales for different kinds of material to be tested.

9. An apparatus for determining the moisture content of different kinds of materials by measuring their conductivity, comprising electrode means connected to a power source for providing a measuring current signal in accordance with the conductivity of the material tested, amplifier means having a low-valued input resistance connected with said electrode means for providing an output in accordance with the measuring voltage signal, an adjustable scale graduated in moisture values, and variable voltage means connected to said adjustable scale for providing a varying voltage with adjustment of said scale to balance the output of the amplifier so as to thereby obtain an indication from said scale of the moisture content of the material tested when balance is achieved.

10. An apparatus according to claim 9, wherein said varible voltage means comprises balancing means for generating a voltage for balancing the output of said amplifier means, said balancing means being connected to said adjustable scale for indicating the moisture value of the tested material in accordance with the balance position of said balancing means, and control element means for indicating deviations in the adjustment of the scale from said balance position.

11. An apparatus according to claim 10, wherein said balancing means includes a potentiometer having a movable member, said scale being coupled with said movable member for indicating on said scale the balance position of said potentimeter which indicates the moisture value of the tested material.

12. An apparatus according to claim 11 further including means for automatically adjusting the potentiometer to the balance position.

13. An apparatus according to claim 11, wherein said automatic adjusting means includes discriminator means for providing an output indicative of the unbalanced condition of said potentiometer and motor means responsive to the output of said discriminator means for adjusting the control member of said potentiometer to a balanced position thereof.

14. An apparatus accordng to claim 11, wherein said potentiometer is manually adjustable to the balanced position.

15. An apparatus according to claim 11, wherein said scale comprises a dial member graduated in percentage moisture values, said dial member being detachably connected to said potentiometer.

16. An apparatus according to claim 15, wherein said dial is further provided with an auxiliary scale for adjusting and monitoring predetermined conditions as an indication of the operability of the apparatus.

17. An apparatus according according to claim 15, wherein a plurality of exchangeable dials are provided corresponding to different materials to be tested, each of said dials being arranged for connection with the potentiometer in predetermined relative position.

18. An apparatus according to claim 15, wherein said dial is provided with a scale on both sides thereof, each scale corresponding to a different material to be tested, said dial being arranged for utilization in said apparatus with either side thereof.

19. An apparatus according to claim 11, wherein said amplifier means includes temperature compensating means for rendering the indication of the moisture content independent of temperature.

20. An apparatus according to claim 9, wherein the measuring signal is a measuring current and said amplifier means includes at its input means for converting the measuring current into a voltage corresponding to the logarithm said current.

21. An apparatus according to claim 20, wherein said electrode means includes a first and a second electrode, said amplifier means includes an operational amplifier having first and second inputs connected respectively to said first and second electrodes, and said means for converting the measuring current to a voltage corresponding to the logarithm of the change in current includes a diode connected between the output and the first input of said amplifier.

22. An apparatus according to claim 21, further comprising temperature compensating means connected between the output and an input of said amplifier for rendering the output of said amplifier independent of temperature.

23. An apparatus according to claim 22, further comprising balancing means for balancing the output of the amplifier, said balancing means being connected to said adjustable scale for indicating the moisture value of the tested material in accordance with the balance position of said balancing means.

24. An apparatus according to claim 23, further comprising control element means for indicating deviations in the adjustment of said scale from the balance position.

* * * * *